United States Patent [19] [11] Patent Number: 4,666,863
Edwards et al. [45] Date of Patent: May 19, 1987

[54] IMMUNOASSAY WITH CHROMATOGRAPHIC MEDIUM AND LABELLED REAGENT

[75] Inventors: John C. Edwards, Little Kingshill; Gerald J. Allen; John K. Martin, both of Wendover; Malcolm R. Summers, Aylesbury, all of England

[73] Assignee: Amersham International plc., Buckinghamshire, England

[21] Appl. No.: 582,591

[22] Filed: Feb. 22, 1984

[30] Foreign Application Priority Data

Feb. 24, 1983 [GB] United Kingdom ............... 8305197

[51] Int. Cl.$^4$ ............... G01N 33/536; G01N 33/543; G01N 33/558; G01N 33/78
[52] U.S. Cl. .................................. 436/514; 436/500; 436/518; 436/533; 436/536; 436/541
[58] Field of Search ............ 436/514, 533, 534, 536, 436/541, 500

[56] References Cited

U.S. PATENT DOCUMENTS

| | | | |
|---|---|---|---|
| 3,843,775 | 10/1974 | Wolf | 436/541 |
| 4,184,849 | 1/1980 | Cambiaso | 436/523 |
| 4,205,058 | 5/1980 | Wagner | 436/541 X |
| 4,235,601 | 11/1980 | Deutsch | 436/514 |
| 4,312,854 | 1/1982 | Derfler | 436/541 X |
| 4,435,504 | 3/1984 | Zuk | 436/810 X |
| 4,446,232 | 5/1984 | Liotta | 435/805 X |

*Primary Examiner*—Sidney Marantz
*Attorney, Agent, or Firm*—Wenderoth, Lind & Ponack

[57] ABSTRACT

A method of performing an assay for an analyte comprises providing a chromatographic medium, preferably in sheet form, forming a reaction mixture containing a labelled reagent present partly in a form which is mobile on the medium and partly in a form which is immobile, the proportions of the two forms being related to the analyte concentration, applying the mixture to a spot on the chromatographic medium, optionally applying a solvent to cause the mobile form of the labelled reagent to migrate from the spot, and measuring the label intensity remaining at the spot. The method provides a convenient way of performing immunoassays, 2-site immunometric assays, and agglutination assays.

8 Claims, No Drawings

IMMUNOASSAY WITH CHROMATOGRAPHIC MEDIUM AND LABELLED REAGENT This invention relates to a method of performing an assay for an analyte in a sample, by forming a reaction mixture containing the sample and a labelled reagent and incubating the mixture so as to partition the reagent between two forms in proportions which depend on the amount of the analyte in the sample. Such assays include the well-known immunoassay, one-site immunometric assay, two-site (or sandwich) immunometric assay, and agglutination assay.

In heterogeneous assays, it is necessary to separate the two forms of labelled reagent, so that the amount or concentration of one can be measured without interference by the other. Various methods of separation have been employed, including precipitation, sedimentation, filtration, centrifugation and decantation. This invention is concerned with another method of separating the two forms of the labelled reagent.

J. L. Giegel et al (Clin. Chem. 28/9, 1894-8 [1982]) describe a radial partition immunoassay in which an antibody to the analyte is immobilised (by a second antibody) at the centre spot of a glass fibre filter paper. The sample containing the analyte is applied to the spot, followed after an incubation step by an enzyme labelled version of the analyte. Then a wash solution is applied to the spot to cause that part of the labelled reagent which has not become bound to the immobilised antibody to migrate from the spot. The wash solution contains a substrate from the enzyme. Finally, the enzyme concentration remaining at the spot is observed by the rate of production of fluoroscent material. Though the system is well adapted for automatic operation, it has a number of weaknesses:

(i) A different set of filter papers is required for each different assay contemplated.

(ii) Care must be taken in the preparation of the filter papers with immobilised antibody because the amount of reactive antibody must be evenly distributed and the same from one filter paper to another.

(iii) It is not possible to add more than one reagent to the filter paper simultaneously. The addition of each reagent must be followed by an incubation period before the addition of the next reagent. Otherwise the first reagent will be washed away from the immobilised antibody by the addition of a subsequent reagent.

(iv) Precautions must be taken to prevent the filter paper becoming dry during the incubation period, particularly when performed at elevated temperatures.

The present invention seeks to overcome these weaknesses.

The invention provides a method of performing an assay for an analyte in a sample which method comprises providing a chromatographic medium, forming a reaction mixture containing a labelled reagent present partly in a form which is mobile on said medium and partly in a form which is immobile on said medium, the proportions of the two forms being determined by the amount of the analyte in the sample, applying the reaction mixture to a spot on the chromatographic medium, causing the mobile form of the labelled reagent to migrate from the spot, and thereafter observing one or both of the mobile and immobile forms of the labelled reagent.

According to the method, a reaction mixture of the sample containing the analyte with the other desired reagents in an aqueous medium is formed and incubated, in several stages if desired. Then, when reaction has gone to completion or has continued for a desired time, all or part of the reaction mixture is applied to a spot on a chromatography medium. Species which are immobile on the medium will remain at the spot, while mobile species will migrate away therefrom. If desired, migration can be assisted by subsequent application of a suitable solvent to the spot. A suitable solvent is one which causes mobile species, but not immobile species to migrate through the chromatography medium. The use of an aqueous liquid is preferred, but organic liquids such as ethanol are possible. If desired, the solvent may be chosen to precipitate one of the forms of the labelled reagent so as to make it immobile in the chromatographic medium.

When migration of the mobile form of the labelled reagent has taken place to a sufficient extent, then either the mobile or the immobile form of the labelled reagent can be observed or measured without interference from the other. Preferably, the mobile form of the labelled reagent is caused to migrate at least 0.5 cm. Preferably, the immobile form of the labelled reagent remaining at the spot is observed or measured.

In the method of the invention, any label can be used which can be used in conventional assays. The most usual classes of labels are radioactive atoms, enzymes, and fluorescent and luminescent materials.

The chromatographic medium used is one on which the two forms into which the labelled reagent has been partitioned have different mobility, so that one form can be physically separated from the other. One form is substantially immobile on the medium, preferably totally immobile, although slight mobility would not necessarily invalidate the method. The medium may be in the form of a column, with the mobile form of the labelled reagent being caused to migrate along it. Preferably, the medium is in the form of a sheet, e.g. of chromatographic paper, with the reaction mixture applied to a spot on it and the mobile form of the labelled reagent being caused to migrate radially from the spot. If the medium is in the form of a wad of paper or a block of material, the mobile form of the labelled reagent may be caused to migrate into the wad or block and so disappear from the surface thereof. Alternatively, a piece of paper or other chromatography medium may be dipped in the reaction mixture, the mobile form of the labelled reagent then being caused to migrate upwards. Alternatively, if one of the forms is magnetically susceptible, it can be made immobile by the application of an external magnetic field, while the non-magnetic form remains mobile.

There are various kinds of assays, all well-known in themselves, where the separation of bound and unbound forms of the labelled reagent can advantageously be effected by chromatographic means.

(a)

Double Antibody Examples

In competition assay, the analyte in the sample, and a labelled version of the analyte, compete for reaction with a limited amount of a specific binder for the analyte. When the analyte is antigenic or a hapten, the specific binder is generally its associated antibody. The analyte/specific binder complex is rendered insoluble by the addition of an antibody (the second antibody) to the specific binder. The specific binder may be reacted with the second antibody before, during or after incubation with the analyte and labelled analyte. When the reaction mixture is applied to a spot on a chromatographic medium, the double antibody complex remains close to the spot while unbound labelled reagent is removed from the spot by subsequent application of a suitable solvent.

(b)

Particulate Solid Phase

Sometimes discrimination between antibody bound labelled reagent and unbound labelled reagent is difficult to achieve by method (a). This may be so with some competition assays for analytes of high molecular weight, or more importantly when immunometric assay systems are used. In such cases the specific binder for the analyte may be attached to a particulate solid phase which is chosen so that, when applied to a spot on the chromatographic medium, the particles do not migrate to any significant extent under the influence of a subsequently applied solvent. Suitable particulate materials are available commercially, and methods of attaching reagents to them are well known. The subsequently applied solvent causes unbound labelled reagent to migrate away from the spot.

This application of the invention is suitable for competition assays e.g. immunoassays; but more particularly for two-site immunometric assays, were the analyte in the sample is caused to bind to an excess of an immobilised specific binder and a labelled specific binder for the analyte is caused to bind to vacant binding sites of the analyte. As is well known, the analyte in the sample can be incubated with the two specific binders (one immobilised, the other labelled) in either order or simultaneously. The amount of labelled reagent bound to the immobilised material is directly proportional to the amount of analyte in the sample.

(c)

Agglutination Reactions

The end point for agglutination can be assessed in a number of ways both visually and by instrumentation. However, at low levels of agglutination, the small number of aggregates may be obscured by the large background of non-agglutinated particles making discrimination difficult and reducing the sensitivity of the assay. Using the method of this invention it is possible to choose the particle characteristics such that when applied to a spot on a chromatography medium, the agglutinated particles remain close to the spot, whereas non-agglutinated particles are removed by a suitable solvent. By using fluorescent or coloured particles it is possible to detect (by eye or instrumentation) the agglutinated particles at the spot in the absence of non-agglutinated particles. In this way, sensitivity is improved. The agglutinated particles may be stabilised prior to separation by chromatography from the unagglutinated particles by using a fixing compound as described in U.S. Pat. No. 4,332,788.

The use of labelled particles in agglutination reactions is known and is described for example in U.S. Pat. Nos. 3,853,987 and 4,332,788. But separation of the two forms of the label by chromatography is not suggested.

The following Examples illustrate the invention.

EXAMPLE 1

[Illustrating method (a)]

Radioimmunoassay for thyroxine

1. The following reagents were incubated together in a series of test tubes for 45 minutes at room tempterature:
   20 µl of a standard solution of thyroxine in human serum.
   50 µl of $^{125}$I-labelled thyroxine in a suitable buffer.
   50 µl of sheep anti-thyroxine serum (gamma globulin fraction) diluted in a TRIS/NaCl buffer.
2. 100 µl of donkey anti-sheep gamma globulin serum diluted in TRIS/NaCl buffer containing 5% PEG 6000 was added to each tube and incubated a further 5 minutes at room temperature.
3. A 100 µl volume was taken from the reaction mixture in each test tube and slowly applied to the centre of a 2.5 cm diameter glass-fibre filter disk (Whatman GF/D) supported at the periphery.
4. A 400 µl volume of TRIS/NaCl buffer was then slowly applied to the centre of each filter disk.
5. The radioactivity remaining at the centre of the filter disks was measured using a gamma scintillation counter collimated so that only the central portion of the disk was exposed to the counter.

| Thyroxine Standard (µg/100 ml) | Percent of total radioactivity remaining at the centre of disk |
| --- | --- |
| 0 | 73.3 |
| 2 | 45.3 |
| 6 | 29.3 |
| 12 | 16.0 |
| 25 | 8.7 |

EXAMPLE 2

[Illustrating method (a)]

Enzyme immunoassay for thyroxine (using a pre-formed second antibody complex)

1. A suspension of antibody complex was formed by mixing suitable amounts of sheep anti-thyroxine serum (gamma globulin fraction) and donkey anti-sheep gamma globulin serum in phosphate buffer and incubating overnight at room temperature.
2. The following reagents were incubated together in a series of test tubes for 2 hours at room temperature.
   100 µl of a standard solution of thyroxine in human serum.
   200 µl of thyroxine conjugated to beta-galactosidase and diluted in phosphate buffer.
   400 µl of the suspension of second antibody complex described above.
3. A 50 µl volume of the reaction mixture from each test tube was then slowly applied to the centre of a glass fibre disk (Whatman GF/D).
4. A 400 µl volume of a 20 mM solution of ONPG (orthonitrophenyl galactoside) in phosphate buffer containing 1 mg bovine serum albumin/ml, 9 mg NaCl/ml and 10 mM magnesium chloride was then slowly applied to the centre of each filter disk.
5. The disks were left for 5 minutes at room temperature before visual observation of the intensity of the yellow spot at the centre of the disk.

| Thyroxine Standard (μg/100 ml) | Intensity of yellow spot |
| --- | --- |
| 0 | +++ |
| 2 | +++ |
| 6 | ++ |
| 12 | + |
| 25 | no colour |

EXAMPLE 3

[Illustrating method (b)]

Radioimmunoassay of thyroxine

1. The following reagents were incubated together in a series of test tubes for 45 minutes at room temperature;
   20 μl of a standard solution of thyroxine in human serum.
   50 μl of $^{125}$I-labelled thyroxine in a suitable buffer.
   100 μl of a suspension of polyvinyl toluene latex particles (2.1μ diameter) coated with sheep anti-thyroxine serum.
2. A 100 μl volume was taken from the reaction mixture in each test tube and slowly applied to the centre of a 2.5 cm prefilter disk (Millipore).
3. A 400 μl volume of TRIS/NaCl buffer was slowly applied to the centre of each filter disk and the radioactivity remaining at the centre of the disk was measured as described in Example 1.

| Thyroxine Standard (μg/100 ml) | Percent of total radioactivity remaining at centre of the disk |
| --- | --- |
| 0 | 93.7 |
| 2 | 52.2 |
| 6 | 33.7 |
| 12 | 17.0 |
| 25 | 15.3 |

EXAMPLE 4

[Illustrating method (b)]

Immunoradiometric assay for human placental lactogen

1. The following reagents were incubated together in a series of test tubes for 30 minutes at room temperature:
   120 μl of a standard solution of HPL in human serum.
   300 μl of a suspension of polystyrene latex particles (0.8μ diameter) coated with sheep anti-HPL serum.
   300 μl of a solution of sheep antibodies to HPL labelled with $^{125}$I.
2. A 100 μl volume was taken from the reaction mixture in each test tube and slowly applied to the centre of a 2.5 cm prefilter disk (Millipore).
3. A 500 μl volume of TRIS/NaCl buffer was slowly applied to the centre of each filter disk and the radioactivity remaining at the centre of the disk was measured as described in Example 1.

| HPL Standard (ng/ml) | Percent radioactivity remaining at the centre of the disk |
| --- | --- |
| 0 | 1.8 |
| 0.14 | 9.5 |
| 0.54 | 23.1 |
| 1.07 | 29.2 |
| 3.3 | 42.5 |
| 9.98 | 45.9 |

EXAMPLE 5

[Illustrating method (b)]

Immunoenzymetric assay of ferritin

1. The following reagents were incubated together in a series of test tubes for 45 minutes at room temperature:
   200 μl of a standard solution of ferritin in phosphate buffer.
   100 μl of a suspension of polystyrene latex particles (0.8μ diameter) coated with sheep anti-ferritin serum.
   200 μl of a solution of sheep antibodies to ferritin conjugated to horseradish peroxidase.
2. A 100 μl volume was taken from the reaction mixture in each test tube and slowly applied to the centre of a 2.5 cm prefilter disk (Millipore).
3. A 500 μl volume of 0.2M acetate buffer, pH 5.0, containing tetramethyl benzidine, hydrogen peroxide and Triton 100 was slowly applied to the centre of each filter disk.
4. The disks were left for 5 minutes before visual observation of the intensity of the blue spot at the centre of each disk. The intensity of colour increased as the standard concentration of ferritin was raised from zero up to 2000 ng/ml. The limit of detection by eye was 30 ng/ml ferritin.

EXAMPLE 6

[Illustration method (c)]

Agglutination assay of ferritin

1. The following reagents were incubated together for one hour at room temperature.
   20 μl of a standard solution of ferritin in phosphate buffer.
   20 μl of a suspension of polystyrene latex particles (1.2μ diameter containing rhodamine fluorescent dye) coated with sheep anti-ferritin serum.
2. 40 μl of a solution of glutaraldehyde in phosphate buffered saline (1% v/v) was added to each reaction tube and incubated for a further 15 minutes at room temperature.
3. After gentle agitation, 50 μl of each reaction mixture was slowly applied to the center of a 2.5 cm glass fibre disk (Whatman GF/D).
4. A 400 μl volume of phosphate buffered saline was slowly applied to the center of each glass fibre disk.
5. The disks were then viewed under ultra-violet light and the intensity of the red fluorescent spot at the center of each disk was observed. The intensity of fluorescence increased as the standard concentration of ferritin was raised. The limit of detection by eye was 15 ng/ml ferritin.

We claim:

1. A method of performing an immunoassay for an analyte in a sample, which method comprises providing a chromatographic medium, forming a reaction mixture containing a specific binder for the analyte and a labelled reagent partly in a form which is mobile on said medium and partly in the form of a labelled analyte/- specific binder reaction product insolubilized so as to be immobile on said medium, the proportions of the two forms being determined by the amount of the analyte in the sample, applying the reaction mixture to a spot on the chromatographic medium, causing the mobile form of the labelled reagent to migrate from the spot, and thereafter observing one or both of the mobile and immobile, insolublized forms of the labelled reagent.

2. The method as claimed in claim 1,
   wherein the chromatographic medium is in sheet form, with the reaction mixture being applied to a spot on the sheet and the mobile form of the labelled reagent being caused to migrate radially from the spot.

3. The method as claimed in claim 1,
   wherein migration is assisted by subsequent application to the spot of a solvent which causes mobile species, but not immobile species, to migrate through the chromatography medium.

4. The method as claimed in claim 3,
   wherein the solvent is an aqueous liquid.

5. The method as claimed in claim 1,
   wherein the reaction mixture is formed by causing the analyte in the sample, and a labelled version of the analyte, to compete for reaction with a limited amount of a specific binder for the analyte, the analyte/specific binder complex being rendered insoluble.

6. The method as claimed in claim 5,
   wherein the analyte/specific binder complex is rendered insoluble by reaction of the specific binder with its antibody, said reaction being effected before, during or after incubation with the analyte and labelled analyte.

7. The method as claimed in claim 1,
   wherein the reaction mixture is formed by causing the analyte in the sample to bind to an excess of an immobilized specific binder and a labelled specific binder for the analyte is caused to bind to vacant binding sites of the analyte.

8. The method as claimed in claim 7,
   wherein the specific binder has been immobilized by attachment to a particulate solid phase.

* * * * *

Notice of Adverse Decisions in Interference

In Interference No. 102,461, involving Patent No. 4,666,863, J. C. Edwards, G. J. Allen, J. K. Martin and M. R. Summers, IMMUNOASSAY WITH CHROMATOGRAPHIC MEDIUM AND LABELLED REAGENT, final judgment adverse to the patentees was rendered July 17, 1991, as to claim 8.
*(Official Gazette August 27, 1991)*